(12) United States Patent
Takahashi et al.

(10) Patent No.: US 8,425,846 B2
(45) Date of Patent: Apr. 23, 2013

(54) SENSING ELEMENT FOR CATALYTIC COMBUSTION TYPE GAS SENSOR

(75) Inventors: Ikuo Takahashi, Tokorozawa (JP); Junji Satoh, Kawagoe (JP)

(73) Assignee: Citizen Holdings Co., Ltd., Tokyo (JP)

( * ) Notice: Subject to any disclaimer, the term of this patent is extended or adjusted under 35 U.S.C. 154(b) by 2006 days.

(21) Appl. No.: 11/092,574

(22) Filed: Mar. 29, 2005

(65) Prior Publication Data

US 2005/0220672 A1 Oct. 6, 2005

(30) Foreign Application Priority Data

Mar. 30, 2004 (JP) ................................ 2004-101538
Jan. 27, 2005 (JP) ................................ 2005-019196

(51) Int. Cl.
*G01N 27/16* (2006.01)
(52) U.S. Cl.
USPC ............................................. 422/95; 422/98
(58) Field of Classification Search ............. 422/94, 422/95, 98; 73/23.31, 25.01
See application file for complete search history.

(56) References Cited

U.S. PATENT DOCUMENTS

| | | | | |
|---|---|---|---|---|
| 4,259,292 A | * | 3/1981 | Ichinose et al. | 422/98 |
| 4,303,612 A | * | 12/1981 | Sonley | 422/94 |
| 4,401,967 A | * | 8/1983 | Miwa et al. | 338/34 |
| 4,464,339 A | * | 8/1984 | Wilkinson-Tough | 422/94 |
| 4,703,646 A | * | 11/1987 | Muller et al. | 73/24.01 |
| 6,576,330 B1 | * | 6/2003 | Schenck et al. | 428/293.4 |
| 7,329,389 B2 | * | 2/2008 | Horovitz et al. | 422/83 |
| 7,713,480 B2 | | 5/2010 | Takahashi et al. | |
| 2010/0175995 A1 | | 7/2010 | Takahashi et al. | |
| 2010/0176094 A1 | | 7/2010 | Takahashi et al. | |

FOREIGN PATENT DOCUMENTS

| | | |
|---|---|---|
| JP | 58-196448 A | 11/1983 |
| JP | 60-15587 A | 1/1985 |
| JP | 60-15587 B2 | 4/1985 |
| JP | 61-82659 A | 4/1986 |
| JP | 61-132564 A | 6/1986 |
| JP | 03-162658 A | 7/1991 |
| JP | 10-50253 A | 2/1998 |
| JP | 11-83781 A | 3/1999 |
| JP | 2002-139469 A | 5/2002 |
| JP | 2005-98405 A | 4/2005 |
| WO | WO 2005-098405 A1 | 10/2005 |

* cited by examiner

*Primary Examiner* — In Suk Bullock
*Assistant Examiner* — Paul Hyun
(74) *Attorney, Agent, or Firm* — Foley & Lardner LLP

(57) ABSTRACT

The catalytic combustion type gas sensor includes a sensing element, a heat conducting layer of which includes boron nitride. The boron nitride content is from 30 wt % to 100 wt % of a material (such as alumina) that would be a base material having the highest proportion in a conventional heat conducting layer without boron nitride. A catalyst layer of the sensing element also includes boron nitride. The boron nitride content is from 10 wt % to 80 wt % of a material (such as tin oxide) that would be a base material having the highest proportion in a conventional catalyst layer without boron nitride.

12 Claims, 9 Drawing Sheets

SENSING ELEMENT FOR CATALYTIC COMBUSTION TYPE GAS SENSOR

BACKGROUND OF THE INVENTION

1) Field of the Invention

The present invention relates to a sensing element for a catalytic combustion type gas sensor.

2) Description of the Related Art

Conventionally, a catalytic combustion type gas sensor is used as a gas sensor to detect flammable gas such as hydrogen and methane. The catalytic combustion type gas sensor includes a Wheatstone bridge circuit. The Wheatstone bridge circuit includes a sensing element, a compensating element, and two resistances.

The sensing element includes a sintered body which is kept at suitable temperature depending on a type of the target gas. On contact with the target gas, the sintered body causes combustion. A part of heat generated by the combustion is transferred to a platinum heater coil, a main part of which is embedded in the sintered body, while the rest of the heat is dissipated into atmosphere. The heat transferred to the heater coil changes temperature of the heater coil, thereby changing resistance of the heater coil. The change in the resistance is output as a voltage change of the sensing element. Thus, the inflammable gas is detected.

A sensing element including a heat conducting layer as the sintered body has been disclosed in, for example, Japanese Patent Application Laid-Open No. H3-162658. The heat conducting layer is made of aluminum nitride combined with alumina, and includes an oxidation catalyst for causing the combustion.

On the other hand, the compensating element is provided to stabilize the output voltage of the gas sensor, by canceling a voltage change of the sensing element due to a temperature change of ambient atmosphere. The compensating element has a similar structure to that of the sensing element. However, the sintered body of the compensating element includes some kind of oxide, instead of the oxidation catalyst, which does not have a combustion activity to the target gas. Therefore, the compensating element does not cause the combustion of the target gas.

With the above structure, the catalytic combustion type gas sensor can alarm a gas leak in the form of output voltage change corresponding to a temperature difference between a temperature due to the combustion and a temperature of ambient atmosphere. However, the above sensing element has the following problem due to low stability of aluminum nitride. That is, when the target gas (such as hydrogen and methane) burns, chemical reaction as shown in equation 1 occurs to generate water vapor. The water vapor reacts with aluminum nitride, thereby decomposing aluminum nitride into alumina and ammonia as shown in equation 2.

$$2H_2 + O_2 \rightarrow 2H_2O \quad (1)$$

$$2AlN + 3H_2O \rightarrow Al_2O_3 + 2NH_3 \quad (2)$$

Catalysis of the oxidation catalyst is temporarily reduced if ammonia exists near the sensing element. As a result, gas sensitivity of the sensing element is temporarily degraded. In addition, such combustion causes a change in a composition of the heat conducting layer gradually from an aluminum nitride base to an alumina base. According to the change, heat conductivity of the heat conducting layer changes, resulting in fluctuation of a zero point of the gas sensor. Thus, it is difficult to commercialize a catalytic combustion type gas sensor including such a sensing element disclosed in Japanese Patent Application Laid-Open No. H3-162658.

The larger a variation of output voltage of the Wheatstone bridge circuit at the same gas concentration is, the higher the gas sensitivity of the gas sensor is. To enhance the gas sensitivity, rate of the heat that is transferred to the heater coil should be increased, while decreasing rate of the heat that is dissipated into atmosphere.

Furthermore, the shorter the time required for the output voltage of the Wheatstone bridge circuit to become stable is, the higher the responsivity of the gas sensor is. To enhance the responsivity, the heat should be transferred to the heater coil through the sintered body as fast as possible.

Moreover, the zero point of the gas sensor should not fluctuate throughout the use of the gas sensor. The sintered body can be further sintered by heat generated by the heater coil to keep the sintered body at a suitable temperature, which changes physical property (such as the heat conductivity) of the sintered body and therefore the zero point of the gas sensor. To avoid the fluctuation of the zero point, the sintered body should be sufficiently sintered at the manufacturing stage, so as not to be further sintered during use of the sensing element.

SUMMARY OF THE INVENTION

It is an object of the present invention to solve at least the above problems in the conventional technology.

A sensing element for a gas sensor according to an aspect of the present invention includes a heater coil, and a sintered body that covers a portion of the heater coil and transfers heat generated by combustion of a target gas to the heater coil. The sintered body includes boron nitride.

A catalytic combustion type gas sensor according to another aspect of the present invention has a Wheatstone bridge circuit with a sensing element and a compensating element serially connected to each other. The sensing element includes a first heater coil, and a first sintered body that includes boron nitride, covers a portion of the first heater coil, and transfers heat generated by combustion of a target gas to the first heater coil. The compensating element includes a second heater coil, and a second sintered body that includes boron nitride, covers a portion of the second heater coil, and transfers surrounding heat to the second heater coil.

The other objects, features, and advantages of the present invention are specifically set forth in or will become apparent from the following detailed description of the invention when read in conjunction with the accompanying drawings.

DETAILED DESCRIPTION

Exemplary embodiments of the present invention will be explained in detail with reference to the accompanying drawings.

Figure 1:
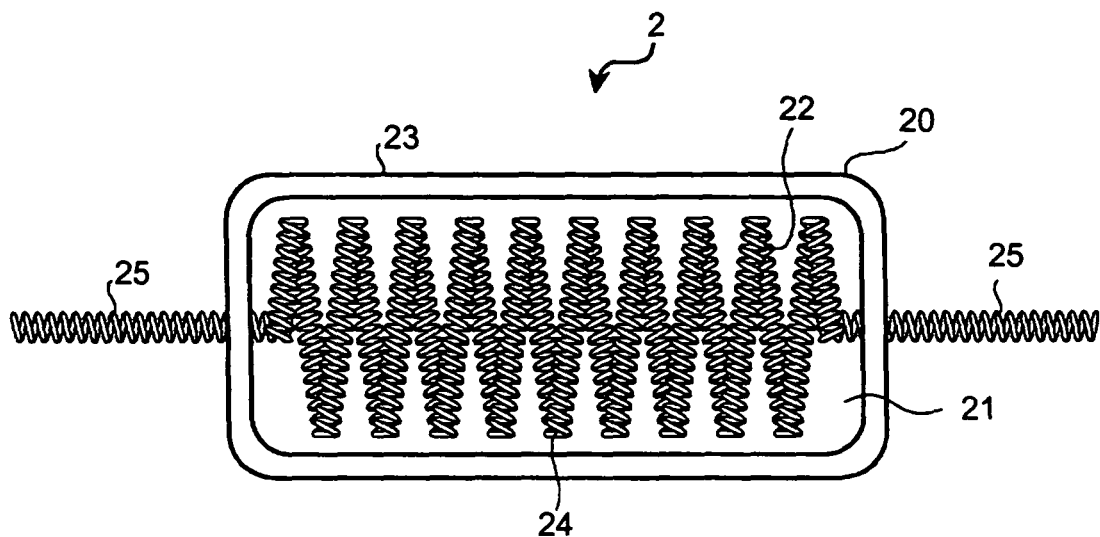
FIG. 1 is a cross section of a sensing element in a catalytic combustion type gas sensor according to a first embodiment of the present invention.

FIG. 1 is a cross section of a sensing element 2 in a catalytic combustion type gas sensor according to a first embodiment of the present invention. The sensing element 2 includes a heater coil 22 and a sintered body 20. The sintered body 20 covers a part of the heater coil 22. The sintered body 20 has, for example, a double layered structure that includes a heat conducting layer 21 and a catalyst layer 23. The heat conducting layer 21 directly covers the heater coil 22, and the catalyst layer 23 is provided on the heat conducting layer 21.

Figure 2:
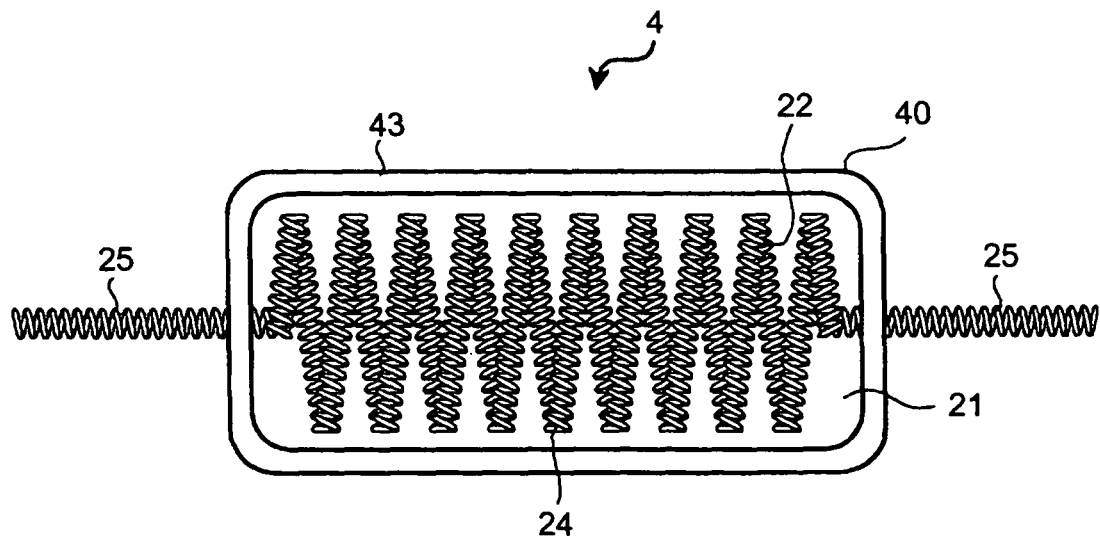
FIG. 2 is a cross section of a compensating element in the catalytic combustion type gas sensor.

FIG. 2 is a cross section of a compensating element 4 that is used in pairs with the sensing element 2 shown in FIG. 1. The compensating element 4 includes the heater coil 22 and a sintered body 40 that covers a part of the heater coil 22. The heater coil 22 of the compensating element 4 has a similar structure to that of the heater coil 22 of the sensing element 2. The sintered body 40 has, for example, a double layered structure that includes the heat conducting layer 21 and a compensating material layer 43. The heat conducting layer 21 directly covers the heater coil 22 in a same manner as the heat conducting layer 21 of the sensing element 2. The compensating material layer 43 is provided on the heat conducting layer 21.

The heat conducting layer 21 is made of, for example, a mixture of alumina (aluminum oxide), titanium oxide, and boron nitride. It is preferable that the heat capacity of the compensating element 4 is equal to that of the sensing element 2, because the compensating element 4 is provided to cancel the variation of the output voltage of the sensing element 2 due to a temperature change of ambient atmosphere. Therefore, it is preferable that the heat conducting layers 21 of the sensing element 2 and the compensating element 4 are same in shape, size, components, and proportions of components, as supposed in the first embodiment.

The boron nitride content of the heat conducting layer 21 is equal to or more than 30 weight percent (wt %) and equal to or less than 100 wt % of a material that would be a base material having the highest proportion in the heat conducting layer 21 if the heat conducting layer 21 did not include boron nitride at all. Unless otherwise specified, the boron nitride content is expressed in a weight percentage with respect to the base material.

A conventional heat conducting layer does not include boron nitride more than an inevitable impurity level. A base material that has the highest proportion in the conventional heat conducting layer is, for example, alumina. Therefore, it is assumed that the base material of the heat conducting layer 21 is also alumina. The heat conducting layer 21 includes boron nitride of between 30 wt % and 100 wt % of the gross weight of alumina included in the conventional heat conducting layer. In other words, in the heat conducting layer 21, 30 wt % to 100 wt % of alumina included in the conventional heat conducting layer is replaced with boron nitride. When the boron nitride content is 100 wt %, alumina is not to be included in the heat conducting layer 21 at all. The boron nitride content explained above can be applied to a heat conducting layer whose base material is not alumina.

The catalyst layer 23 is made of, for example, a mixture of tin oxide, platinum, palladium, and boron nitride. The boron nitride content of the catalyst layer 23 is equal to or more than 10 wt % and equal to or less than 80 wt % of a material that would be a base material having the highest proportion in the catalyst layer 23 if the catalyst layer 23 did not include boron nitride at all.

A conventional catalyst layer does not include boron nitride more than an inevitable impurity level. A base material that has the highest proportion in the conventional catalyst layer is, for example, tin oxide. Therefore, it is assumed that the base material of the catalyst layer 23 is also tin oxide. The catalyst layer 23 includes boron nitride of between 10 wt % to 80 wt % of the gross weight of tin oxide included in the conventional catalyst layer. In other words, in the catalyst layer 23, 10 wt % to 80 wt % of tin oxide included in the conventional catalyst layer is replaced with boron nitride. The boron nitride content explained above can be applied to a catalyst layer whose base material is not tin oxide.

The compensating material layer 43 is made of, for example, a mixture of tin oxide and boron nitride. It is preferable that the compensating material layer 43 has the same thickness as the catalyst layer 23 to equalize heat capacities of the sensing element 2 and the compensating element 4. Moreover, it is preferable that the compensating material layer 43 includes the same materials (except for platinum and palladium) at the same proportions as the catalyst layer 23.

In the first embodiment, the compensating material layer 43 has the same thickness, and includes the same material (except for platinum and palladium) at the same proportions as the catalyst layer 23. Accordingly, the boron nitride content of the compensating material layer 43 is equal to or more than 10 wt % and equal to or less than 80 wt % of a material that would be a base material having the highest proportion in the compensating material layer 43 if the compensating material layer 43 does not include boron nitride at all.

The sensing element 2 is manufactured as follows. A mixed powder of the materials to form the heat conducting layer 21 is added with a solvent and a binder, and kneaded into slurry to be applied to the heater coil 22. Then, a mixed powder of the materials to form the catalyst layer 23 is added with a solvent and a binder, and kneaded into slurry to be applied to the surface of the dried heat conducting layer 21. Then, power is supplied to the heater coil 22 to generate heat for sintering the heat conducting layer 21 and the catalyst layer 23. Although materials are different, the compensating element 4 is manufactured in a same manner as the sensing element 2.

The heat generated by the heater coil is sufficiently transferred to the heat conducting layer 21, the catalyst layer 23, and the compensating material layer 43, because the layers respectively include boron nitride with high heat conductivity. Therefore, the heat conducting layer 21, the catalyst layer 23, and the compensating material layer 43 can be sintered efficiently and uniformly in a short time at the manufacturing stage, without being further sintered even though the sensing element 2 is heated up to the suitable temperature, for example, approximately 450 degree Celsius (° C.) to detect the target gas. Accordingly, physical properties of the heat conducting layer 21, the catalyst layer 23, and the compensating material layer 43 hardly change during the use of the gas sensor, and the zero point fluctuation of the gas sensor with time is small.

As shown in FIGS. 1 and 2, the heater coil 22 includes a bead section 24 and a lead section 25. The bead section 24 is embedded in the sintered body 20 or 40. The lead section 25 is arranged at each end of the bead section 24. The bead section 24 is made up with, for example, a coiled coil. The lead section 25 is made up with, for example, a single coil. The heater coil 22 is manufactured as follows. First, a single coil is formed by coiling an uncoiled platinum wire, a platinum-based alloy wire (such as a wire of a platinum rhodium alloy), or an iron-palladium alloy wire around a core. Then, a part of the single coil is coiled around another core to form a double-coiled coil, that is, the bead section 24.

The lead section 25 can be formed in a double-coiled coil or more while forming the bead section 24 in a triple-coiled coil or more. For example, when the lead section 25 is a double-coiled coil and the bead section 24 is a triple-coiled coil, a single coil is coiled as a primary base coil around a core to form a double-coiled coil, and a part of the double-coiled coil is coiled as a secondary base coil around another core to form a triple-coiled coil. The number of coiled structures in the bead section 24 and the lead section 25 can be increased by increasing the number of coiling procedures.

Figure 3:
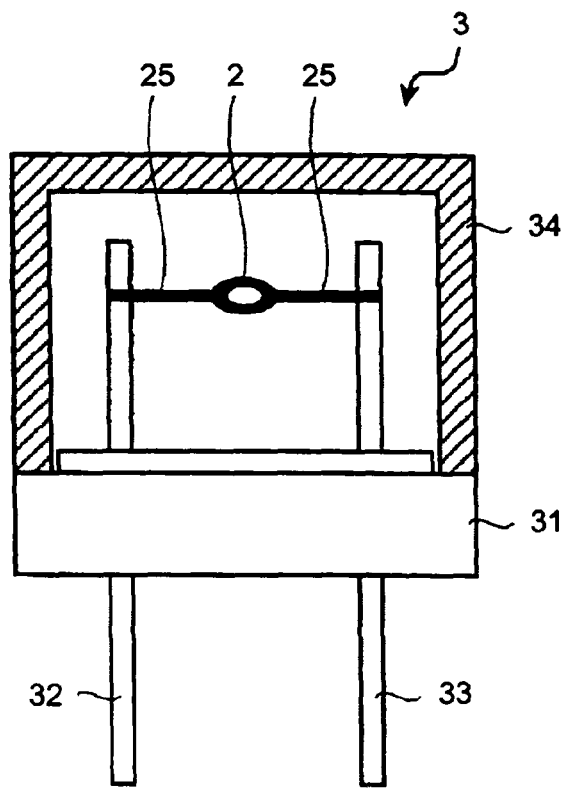
FIG. 3 is a cross section of a sensor in the catalytic combustion type gas sensor.

FIG. 3 is a cross section of a sensor unit 3 in the catalytic combustion type gas sensor according to the first embodiment. As shown in FIG. 3, the sensor unit 3 includes a mount base 31 made of ceramics or resin, and pin electrodes 32 and 33 piercing through the mount base 31 and connecting the sensor unit 3 with an external device. The lead sections 25 at both ends of the sensing element 2 and the compensating element 4 (not shown in FIG. 3) are respectively connected to the pin electrodes 32 and 33. The sensing element 2 and the compensating element 4 are surrounded by the mount base 31 and an explosion-proof structure 34.

Figure 4:
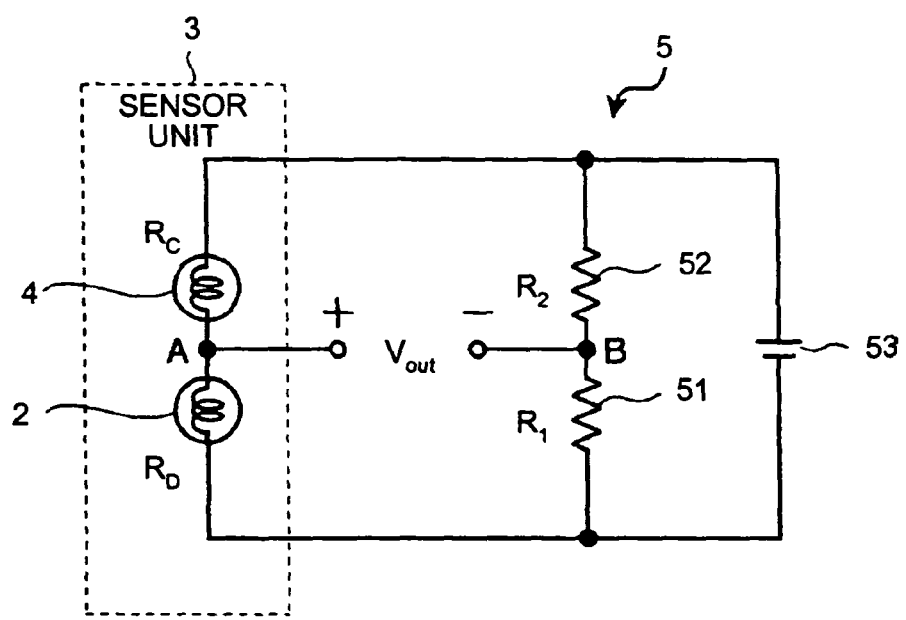
FIG. 4 is a circuit diagram of the catalytic combustion type gas sensor.

FIG. 4 is a circuit diagram of a catalytic combustion type gas sensor 5 according to the first embodiment. The catalytic combustion type gas sensor 5 includes the sensing element 2, the compensating element 4 that is connected to the sensing element 2 in series, a first resistor 51, a second resistor 52 that is connected to the first resistor 51 in series, and a power source (power source circuit) 53 that applies a direct current to the above components. The sensing element 2, the compensating element 4, the first resistor 51, and the second resistor 52 form a Wheatstone bridge circuit which outputs the difference between the voltage at a point A (which is located between the sensing element 2 and the compensating element 4) and the voltage at a point B (which is located between the first resistor 51 and the second resister 52). An output voltage $V_{out}$ of the Wheatstone bridge circuit is 0 volt (V) when $R_C \times R_1 = R_D \times R_2$, where $R_D$, $R_C$, $R_1$, and $R_2$ are the resistances of the sensing element 2, compensating element 4, the first resistor 51, and the second resistor 52, respectively.

The heater coils 22 supplied with a rated voltage from the power source 53 generate heat to bring the sensing element 2 and the compensating element 4 to the suitable temperature for detecting the target gas. The terminal temperatures of the sensing element 2 and the compensating element 4 determine the resistances of the above components, and therefore the output voltage $V_{Out}$ of the Wheatstone bridge circuit. The combustion of the target gas increases the resistance $R_D$ of the sensing element 2, and therefore the output voltage $V_{out}$ in a positive direction according to the gas sensitivity.

The inventors conducted tests to evaluate response speed, gas responsivity, and stability of the zero point with time of the catalytic combustion type gas sensor 5. Results of a test for the response speed are shown in table 1. The test was conducted with several samples. The samples are catalytic combustion type gas sensors in which only the heat conducing layers 21 of the sensing element 2 and the compensating element 4 include boron nitride, while the catalyst layer 23 and the compensating material layer 43 do not include boron nitride. The boron nitride content of the heat conducting layer 21 varies in each of the samples. Response time shown in table 1 is time required for an output value of the catalytic combustion type gas sensor to reach 90 percent (%) of a stable value in a hydrogen gas of 4,000 parts per million (ppm). A sample of which the boron nitride content is 0 wt % is a catalytic combustion type gas sensor that includes a conventional sensing element and a conventional compensating element that do not include boron nitride in the heat conducting layer, the catalyst layer, and the compensating material layer.

TABLE 1

| | Boron nitride content (wt %) | | | | | | | | |
|---|---|---|---|---|---|---|---|---|---|
| | 0 | 30 | 40 | 50 | 60 | 70 | 80 | 90 | 100 |
| Response time (second) | 5.0 | 4.0 | 3.0 | 2.0 | 2.0 | 2.0 | 1.5 | 1.5 | 1.5 |

As shown in table 1, when the boron nitride content is equal to or more than 30 wt %, the higher the content is, the shorter the response time becomes. On the other hand, reduction in the response time when the content is less than 30 wt % should be considered as an error. Therefore, appropriate boron nitride content is from 30 wt % to 100 wt %.

Results of another test for the response speed are shown in table 2. The test was conducted with several samples. The samples are catalytic combustion type gas sensors in which only the catalyst layer 23 and the compensating material layer 43 include boron nitride, while the heat conducting layer 21 does not include boron nitride. The boron nitride content of the catalyst layer 23 and the compensating material layer 43 varies in each of the samples. Response time shown in table 2 is time required for an output value of the catalytic combustion type gas sensor to reach 90% of a stable value in a hydrogen gas of 4,000 ppm. A sample of which the boron nitride content is 0 wt % is a catalytic combustion type gas sensor that includes a conventional sensing element and a conventional compensating element that do not include boron nitride in the heat conducting layer, the catalyst layer, and the compensating material layer.

TABLE 2

| | Boron nitride content (wt %) | | | | | | |
|---|---|---|---|---|---|---|---|
| | 0 | 30 | 40 | 50 | 60 | 70 | 80 |
| Response time (second) | 5.0 | 4.5 | 3.5 | 3.0 | 3.0 | 3.0 | 3.0 |

As shown in table 2, when the boron nitride content is equal to or more than 30 wt %, the higher the content is, the shorter the response time becomes. On the other hand, reduction in the response time when the content is less than 30 wt % should be considered as an error. By comparing the results shown in table 1 and the results shown in table 2, it is found that the response time can be more effectively reduced when boron nitride is included in the heat conducting layers 21, which constitutes most of the sensing element 2 and the compensating element 4.

Results of a test for the gas sensitivity are shown in table 3. The test was conducted with several samples. The samples are catalytic combustion type gas sensors, and the boron nitride content of the catalyst layer 23 and the compensating material layer 43 varies in each of the samples. The gas sensitivity shown in table 3 is a difference between an output voltage in a hydrogen gas of 4,000 ppm and an output voltage in normal air, which is expressed as a relative value with respect to the gas sensitivity of the sample including 0 wt % boron nitride.

TABLE 3

| | Boron nitride content (wt %) | | | | | | | | | |
|---|---|---|---|---|---|---|---|---|---|---|
| | 0 | 1 | 5 | 10 | 20 | 30 | 40 | 50 | 60 | 80 |
| Sensitivity to $H_2$ (a.u.) | 100 | 100 | 103 | 105 | 110 | 90 | 80 | 70 | 60 | 40 |

As shown in FIG. 3, the sample including 10 wt % or 20 wt % boron nitride has significantly high gas sensitivity as compared to the sample including 0 wt % boron nitride. However, the samples including 30 wt % or more boron nitride have the gas sensitivity lower than the sample including 0 wt % boron nitride, because the combustion activity of the catalyst in the catalyst layer 23 is decreased. The sample including 80 wt % boron nitride can be introduced to the actual use even though the gas sensitivity decreases to about 40%. However, it is not preferable that the boron nitride content exceeds 80 wt % because the gas sensitivity seriously becomes low.

Considering both the results shown in table 2 and the results shown in table 3, appropriate boron nitride content of the catalyst layer 23 and the compensating material layer 43 is equal to 10 wt % or more and equal to 80 wt % or less. However, if the boron nitride content is equal to 10 wt % or more and less than 30 wt %, significant effect in the response speed cannot be expected.

An accelerated test under an overvoltage of 140% rated voltage was conducted to evaluate the fluctuation of the zero point with time. In the test, 10 samples including 50 wt % boron nitride in the heat conducting layers 21 of the sensing element 2 and the compensating element 4, and another 10 samples including no boron nitride were used. A value of each of the 10 samples is converted into a hydrogen concentration, and an average value of the 10 samples is shown in table 4. As shown in table 4, the fluctuation of the samples with boron nitride is smaller, and is 50% to 60% of that of the samples without boron nitride.

TABLE 4

| | Accelerated elapsed-time (days) | | | | | |
|---|---|---|---|---|---|---|
| | 0 | 15 | 30 | 60 | 90 | 120 |
| Sample including 50 wt % boron nitride (ppm) | 0 | ±30 | ±100 | ±150 | ±250 | ±300 |
| Sample without boron nitride (ppm) | 0 | ±50 | ±150 | ±300 | ±450 | ±500 |

The higher the resistance of the heater coil is, the higher voltage is to be required for the power source to obtain the suitable temperature. Therefore, the higher the resistance of the heater coil is, the higher the gas sensitivity of the gas sensor becomes, because the output voltage $V_{out}$ of the Wheatstone bridge circuit is proportional to the voltage of the power source. The heater coil 22, whose bead section 24 is a coiled-coil as shown in FIGS. 1 and 2, can achieve higher gas sensitivity than a heater coil whose bead section is a single coil, because the coiled-coil has higher resistance than the single coil.

Figure 5:
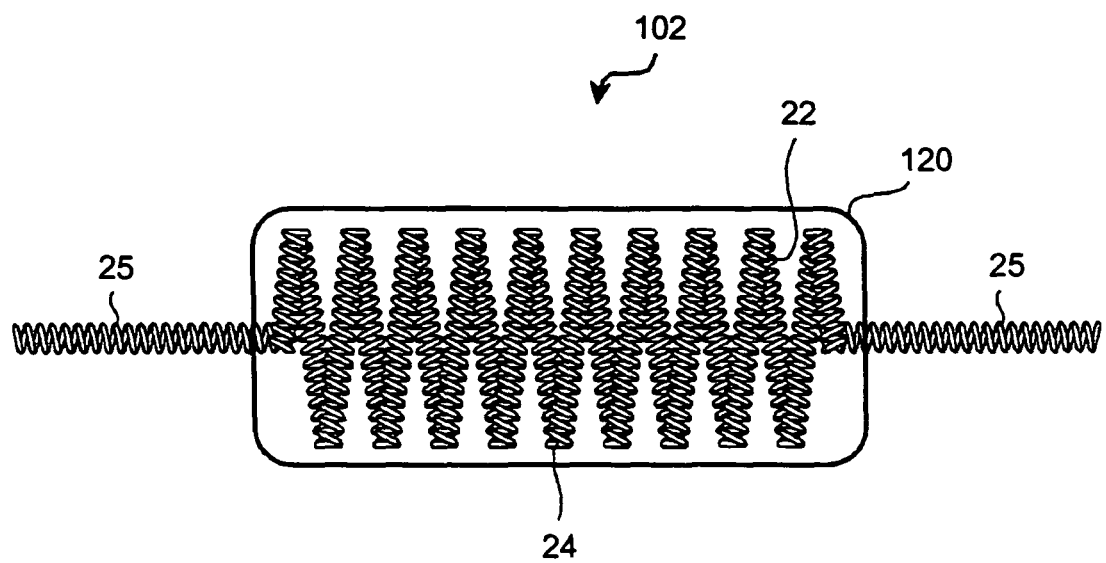
FIG. 5 is a cross section of a variation of the sensing element.
Figure 6:
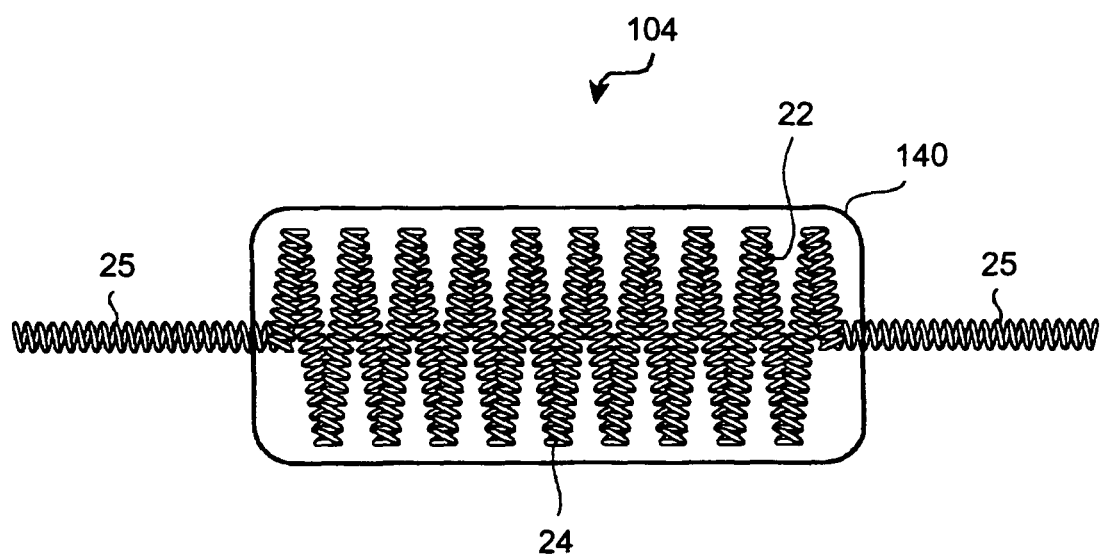
FIG. 6 is a cross section of another variation of the compensating element.

Moreover, a sensing element 102 and a compensating element 104 shown in FIGS. 5 and 6 can be used instead of the sensing element 2 and the compensating element 4. A sintered body 120 of the sensing element 102 has a single layer structure and made of a mixture of a catalyst and a heat conducting material. A sintered body 140 of the compensating element 104 has a single layer structure and made of a mixture of a compensating material and the heat conducting material. With the sensing element 102 and the compensating element 104, it is possible to obtain a same effect as the effect obtained with the sensing element 2 and the compensating element 4.

Figure 7:
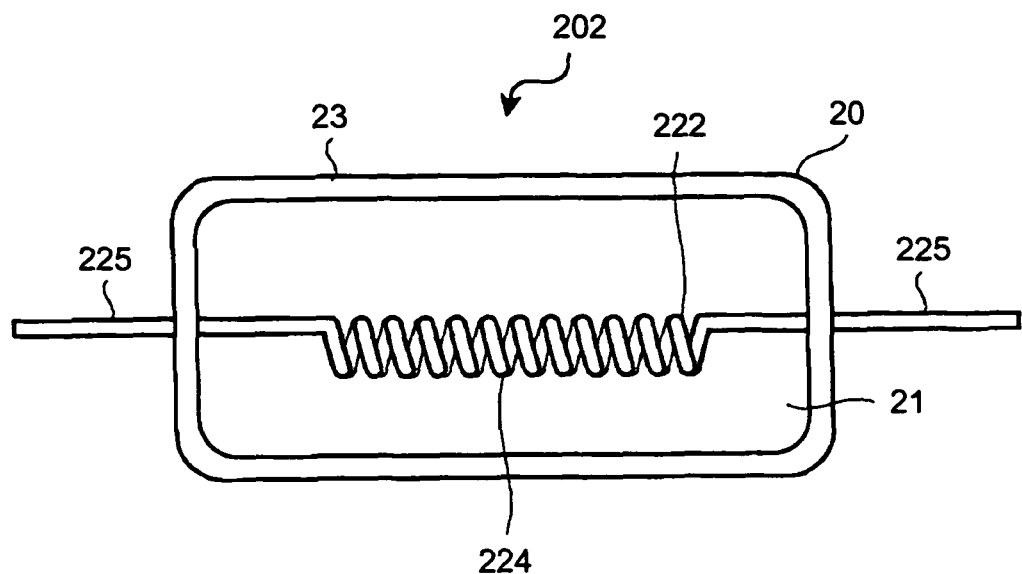
FIG. 7 is a cross section of still another variation of the sensing element.
Figure 8:
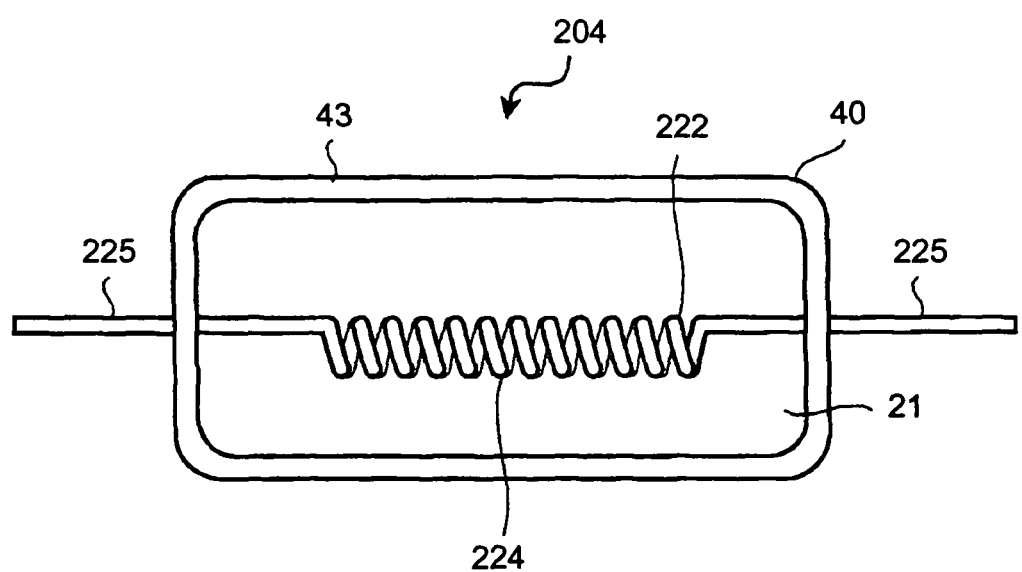
FIG. 8 is a cross section of still another variation of the compensating element.

Alternately, a sensing element 202 and a compensating element 204, which include a heater coil 222 as shown in FIGS. 7 and 8, can be used instead of the sensing element 2 and the compensating element 4. A bead section 224 of the heater coil 222 is a single coil while a lead section 225 thereof being an uncoiled wire.

Figure 9:
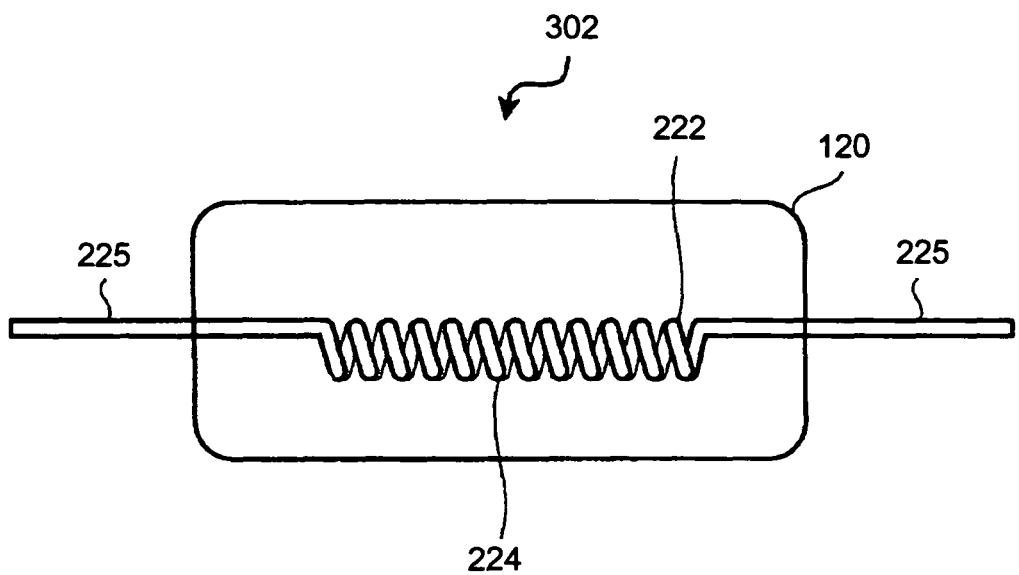
FIG. 9 is a cross section of still another variation of the sensing element.
Figure 10:
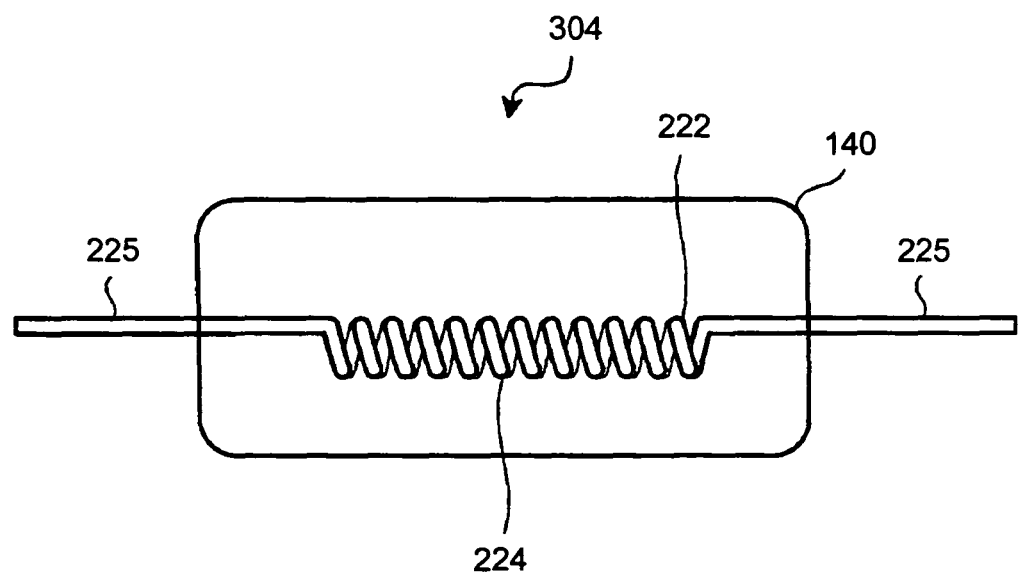
FIG. 10 is a cross section of still another variation of the compensating element.

Alternately, a sensing element 302 and a compensating element 304 shown in FIGS. 9 and 10 can be used instead of the sensing element 2 and the compensating element 4. The sensing element 302 includes the heater coil 222 and the sintered body 120 having the single layer structure. The compensating element 304 includes the heater coil 222 and the sintered body 140 having the single layer structure.

Figure 11:
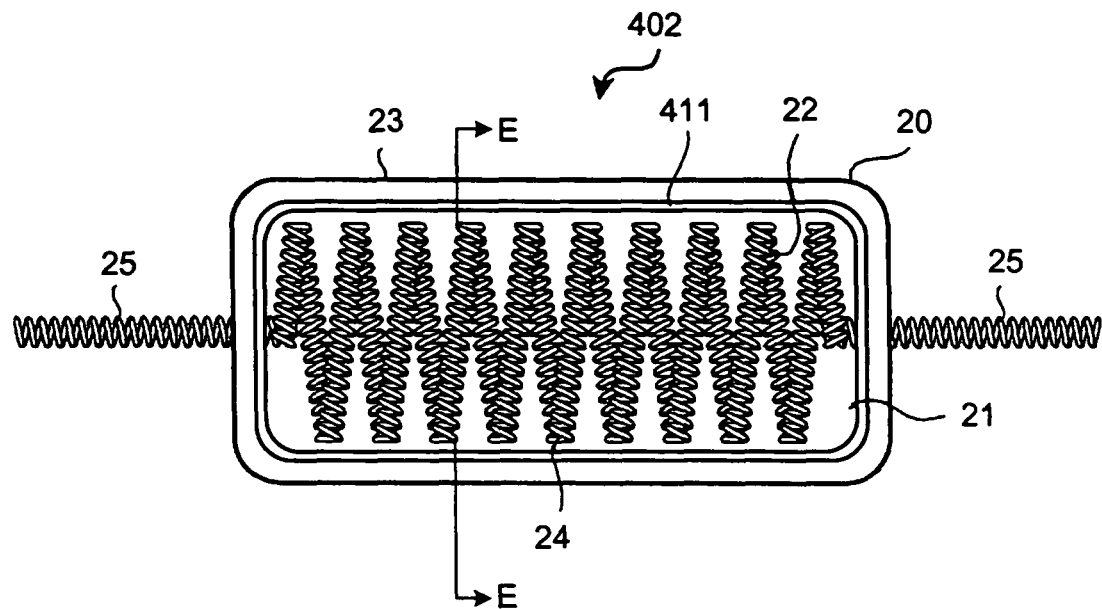
FIG. 11 is a cross section of a sensing element in a catalytic combustion type gas sensor according to a second embodiment of the present invention.
Figure 12:
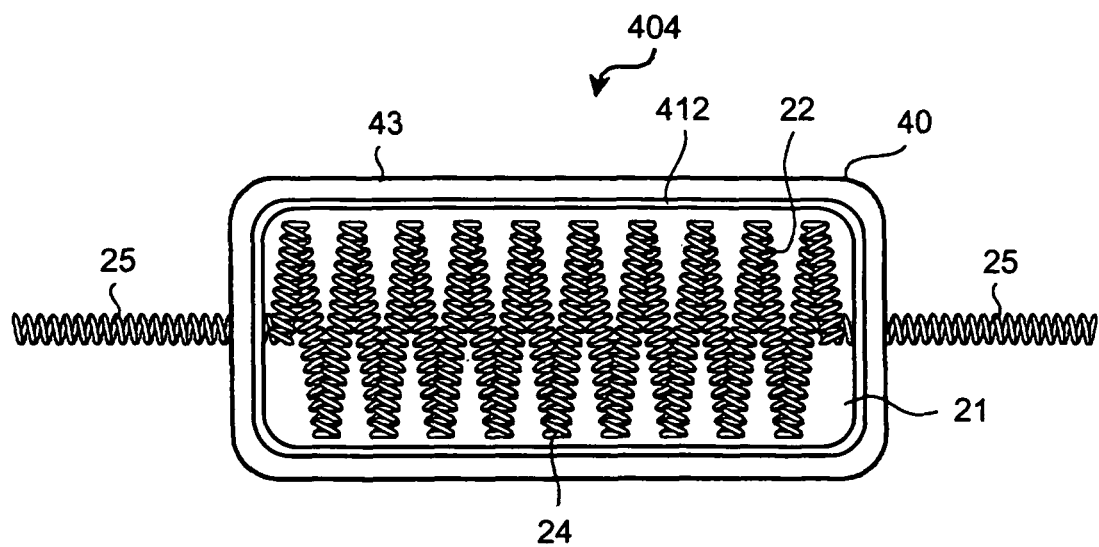
FIG. 12 is a cross section of a compensating element in the catalytic combustion type gas sensor.

FIGS. 11 and 12 are cross sections of a sensing element 402 a compensating element 404 according to a second embodiment of the present invention. As shown in FIG. 11, the sensing element 402 includes a first intermediate layer 411 between the heat conducting layer 21 and the catalyst layer 23. As shown in FIG. 12, the compensating element 404 includes a second intermediate layer 412 between the heat conducting layer 21 and the compensating material layer 43. Other structures in the sensing element 402 and the compensating element 404 are the same as those of the sensing element 2 and the compensating element 4 according to the first embodiment. Like reference numerals refer to like parts, and redundant explanation is omitted.

The first intermediate layer 411 includes a combustion catalyst for causing combustion of the target gas, that is, noble metal such as platinum, palladium, rhodium, and iridium, and oxides thereof. In other words, the first intermediate layer 411 includes the combustion catalyst, which is also included in the catalyst layer 23, in high concentration, and has a high combustion activity. Concentration of the combustion catalyst in the catalyst layer 23 according to the second embodiment is lower than that according to the first embodiment.

Figure 13:
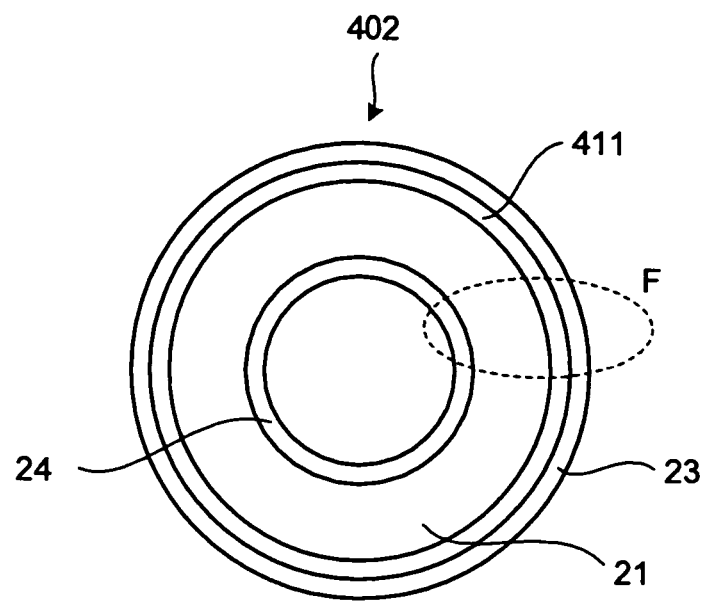
FIG. 13 is cross section of the sensing element cut along a line E-E shown in FIG. 11.
Figure 14:
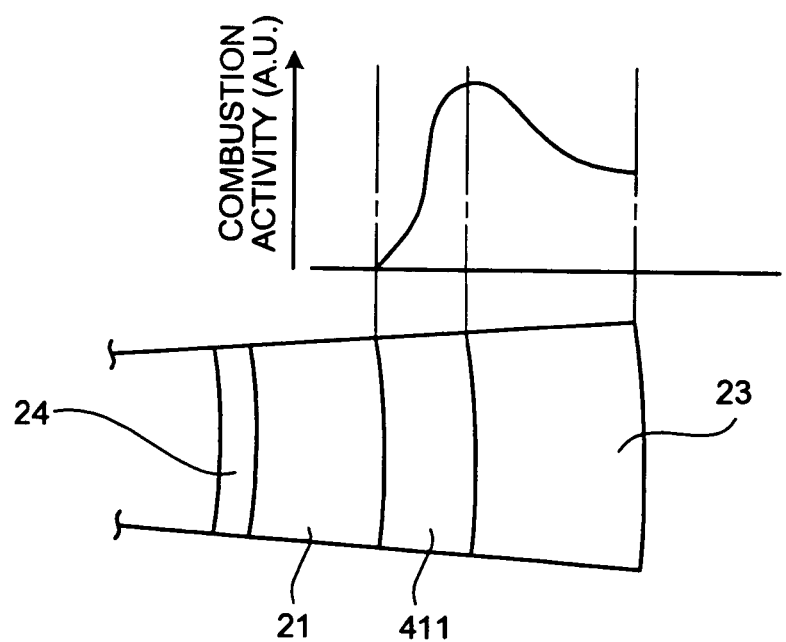
FIG. 14 is a characteristic plot of combustion activity of the sensing element shown in FIG. 11.

FIG. 13 is a cross section of the sensing element 402 cut along a line E-E shown in FIG. 11. FIG. 14 is a magnified view and a characteristic plot of combustion activity of a portion F shown in FIG. 13. As shown in FIG. 14, the combustion activity is highest near the interface between the first intermediate layer 411 and the catalyst layer 23 because the concentration of the combustion catalyst is higher in the first intermediate layer 411 than in the catalyst layer 23 as described above.

Figure 15:
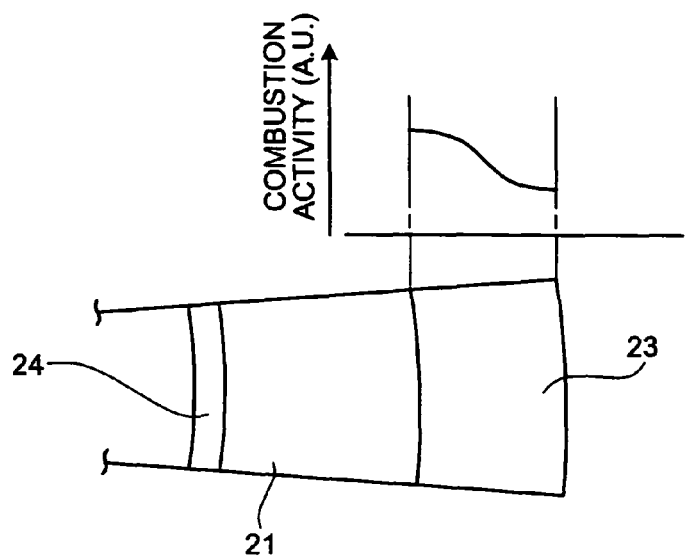
FIG. 15 is a characteristic plot of combustion activity of a sensing element without an intermediate layer.

On the other hand, FIG. 15 is a characteristic plot of combustion activity of a portion, which corresponds to the portion F, of a sensing element without the first intermediate layer 411. As shown in FIGS. 14 and 15, both of the sensing elements have the gas sensitivity only at the outer layer of the heat conducting layer 21. However, in the sensing element 402 with the first intermediate layer 411, the outer interface of the heat conducting layer 21 is nearer to the bead section 24 than in the sensing element without the first intermediate layer 411. Therefore, in the sensing element 402, the combustion of the flammable gas can be caused at a portion closer to the bead section 24 than in the sensing element without the first intermediate layer 411.

Stable supply of oxygen is essential for the catalytic combustion of the flammable gas. In the second embodiment, oxygen is supplied from oxide, such as tin oxide, in the catalyst layer 23. Oxygen on an interface between tin oxide and the combustion catalyst (such as platinum) is also supplied for the catalytic combustion.

The second intermediate layer 412 is provided in the compensating element 404 to equalize thermal properties, such as heat capacities, of the sensing element 402 and the compensating element 404. The second intermediate layer 412 can also prevent an undesired small combustion in the compensating element 404, which sometimes occurs in a conventional compensating element when a target gas is highly concentrated. The second intermediate layer 412 is made of a material, such as copper oxide, that does not have combustion activity to the target gas.

The sensing element 402 that includes the first intermediate layer 411 is manufactured as follows. Slurry of materials of the heat conducting layer 21 is applied to the heater coil 22, and dried. A chloride solution or an acetate solution of noble metal/noble metals, at least concentration of which is controlled, is further applied to the dried surface. The chloride solution or the acetate solution can include a plurality of noble metals such as platinum, palladium, rhodium, iridium, and ruthenium in an appropriate combination, or exclusively include any of the noble metals. Next, slurry of materials of the catalyst layer 23 is applied to the dried surface. Then, power is supplied to the heater coil 22 to generate heat for sintering the heat conducting layer 21, the first intermediate layer 411, and the catalyst layer 23.

The compensating element 404 that includes the second intermediate layer 412 is manufactured as follows. The slurry of materials of the heat conducting layer 21 is applied to the heater coil 22, and dried. A solution of copper sulfate or copper acetate, at least concentration of which is controlled, is further applied to the dried surface. Next, slurry of materials of the compensating material layer 43 is applied to the dried surface. Then, power is supplied to the heater coil 22 to generate heat for sintering the heat conducting layer 21, the second intermediate layer 412, and the compensating material layer 43.

The catalytic combustion type gas sensor that includes the sensing element 402 and the compensating element 404 is expected to have improved gas sensitivity, improved immunity to external factors of degrading the gas sensitivity, and improved sulfur oxide (SOx) resistance.

The gas sensitivity is dependent on concentration of the combustion catalyst. The concentration of the combustion catalyst in the sensing element 402 is higher than that of the sensing element 202, because the sensing element 402 includes the first intermediate layer 411. Therefore, the sensing element 402 has higher gas sensitivity than that of the sensing element 202.

Figure 16:
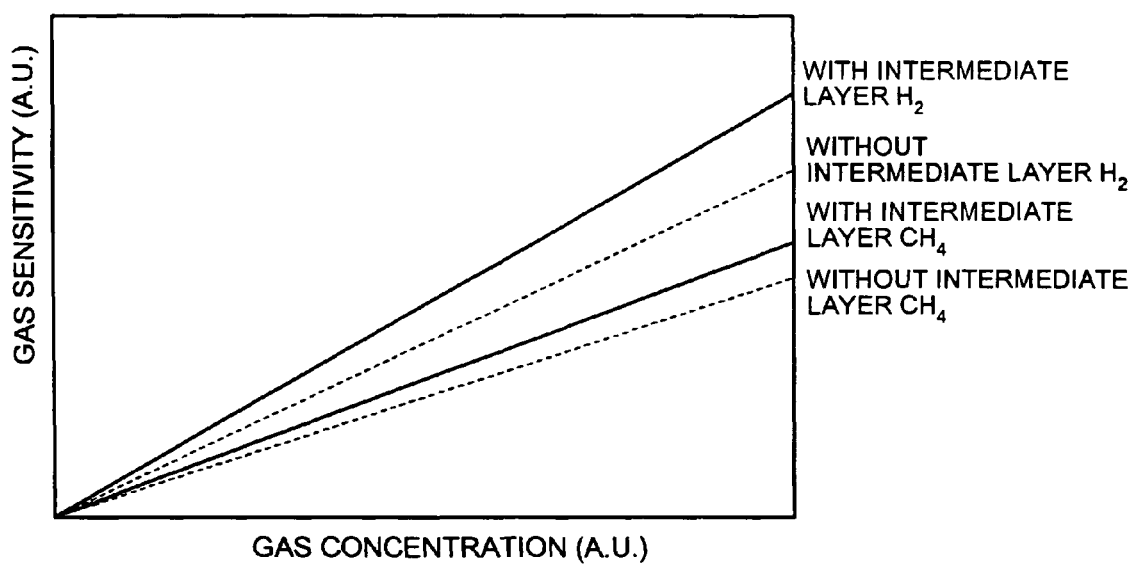
FIG. 16 is a graph of gas sensitivity of the sensing element shown in FIG. 11 and the sensing element without the intermediate layer.

FIG. 16 is a graph of the gas sensitivity of the sensing element 402 that includes the first intermediate layer 411 and a sensing element without an intermediate layer. As shown in FIG. 16, the sensing element 402 has higher gas sensitivity to any of hydrogen and methane by about 20% than that of the sensing element without the intermediate layer. Moreover, especially to methane, individual difference in the gas sensitivity of the sensing element 402 (that is, fluctuation in the gas sensitivity among a plurality of sensing elements 402) is decreased.

There are various factors of degrading the gas sensitivity in an environment in which the catalytic combustion type gas sensor is actually used. For example, a high polymer organic substance, such as oil steam generated in a kitchen, causes incomplete combustion in the catalyst layer 23. Carbon generated by the incomplete combustion tends to accumulate at the catalyst layer 23, which is the outermost portion of the sensing element and in which the temperature of the catalyst is low. In the sensing element without the intermediate layer, the catalytic combustion of the flammable gas occurs only in the catalyst layer. Therefore, the gas sensitivity is gradually degraded due to accumulation of such carbon. On the other hand, in the sensing element 402, the catalytic combustion of the flammable gas is also caused in the first intermediate layer 411. Therefore, even if the gas sensitivity is degraded to some extent, a rate of degradation is low.

Furthermore, when the catalytic combustion type gas sensor is used for an exhaust gas of an automobile engine including SOx for several ppm, a material included in a sensing element or a compensating element tends to be temporarily sulfurized (accumulation of sulfur). The sulfurized material is never reduced as long as it is exposed to the exhaust gas, even though it is reduced in a normal air by heat generated by the heater coil. As a result, the zero point of the gas sensor fluctuates.

In the sensing element, the combustion catalyst causes oxidation of SOx to slow down the accumulation. On the other hand, the combustion does not occur in the compensating element. Therefore, the accumulation tends to be prominent in the compensating element, even though it is exposed to the same gas as the sensing element. However, after a certain point in time, rate of the accumulation of sulfur in the compensating element becomes similar to that in the sensing element, although it proceeds rapidly at an early stage. Therefore, the fluctuation of the zero point hardly occurs after a predetermined time has passed.

Figure 17:
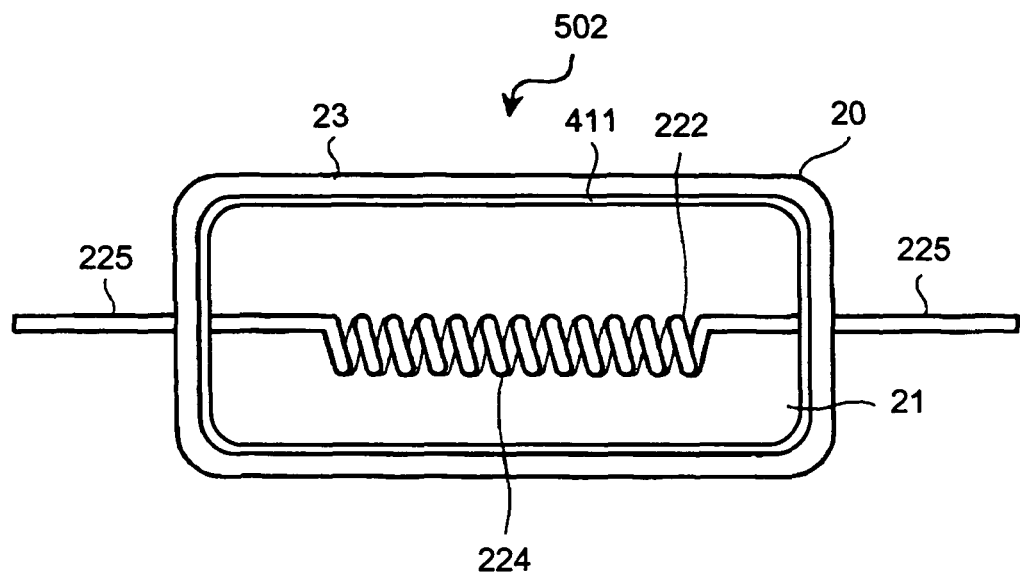
FIG. 17 is a cross section of a variation of the sensing element.
Figure 18:
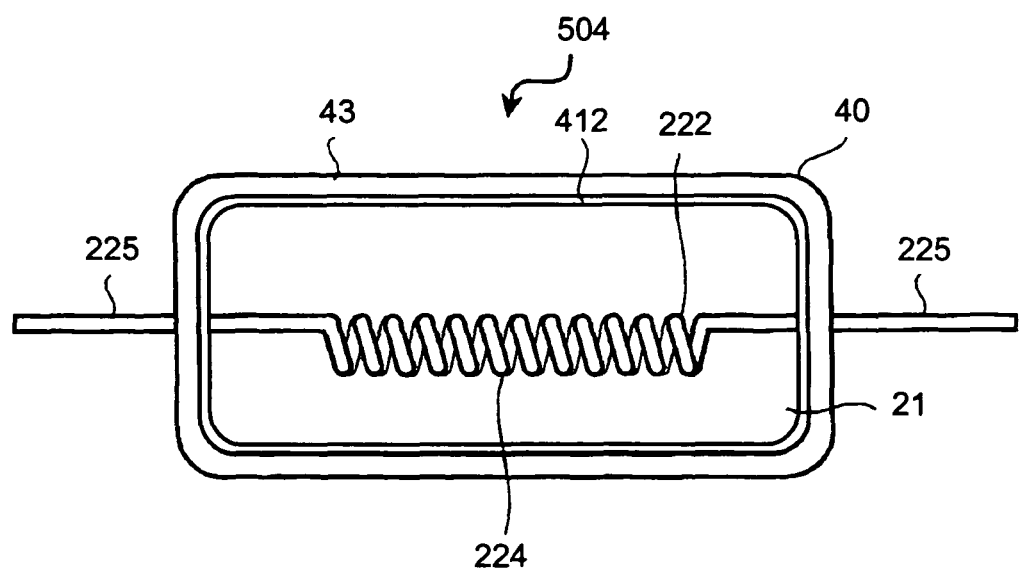
FIG. 18 is a cross section of a variation of the compensating element.

In the second embodiment, the compensating element 404 is manufactured so that it contains as much sulfur as to saturate the fluctuation of the zero point. For example, the compensating element 404 is made from copper sulfide, which is decomposed into copper oxide, sulfur trioxide, and the like at temperature higher than 600° C. As a result, even if sulfur further accumulates during use, further fluctuation of the zero point does not occur. Therefore, it is possible to realize a stable gas sensor without the fluctuation of the zero point. It is possible to obtain a similar effect with a sensing element 502 and a compensating element 504 shown in FIGS. 17 and 18, which include the heater coil 222 of which the lead section 225 is left uncoiled and the bead section 224 is a single coil.

The present invention is not limited to the embodiments described above, and various modifications can be made. For example, as long as the heat conducting layer 21, the catalyst layer 23, and the compensating material layer 43 include boron nitride, other components can be changed depending on a type of a target gas.

According to the present invention, a catalytic combustion type gas sensor with high gas sensitivity can be realized.

Moreover, according to the present invention, a catalytic combustion type gas sensor with fast response time can be realized.

Furthermore, according to the present invention, a catalytic combustion type gas sensor with small fluctuation of a zero point can be realized.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A sensing element for a catalytic combustion type gas sensor comprising:
   a heater coil; and
   a sintered body that covers a portion of the heater coil and transfers heat generated by combustion of a target gas in the catalytic combustion type gas sensor to the heater coil, wherein
   the sintered body includes:
      a catalyst layer for causing the combustion;
      a heat conducting layer that transfers the heat to the heater coil; and
      an intermediate layer between the catalyst layer and the heat conducting layer, and wherein combustion activity of the sensing element is highest near an interface between the intermediate layer and the catalyst layer, wherein the intermediate layer includes the same combustion catalyst as the catalyst layer at a higher concentration than the catalyst layer.

2. The sensing element according to claim 1, wherein the sintered body includes boron nitride.

3. The sensing element according to claim 2, wherein boron nitride content is 30 weight percent or more and 100 weight percent or less of a gross weight of the boron nitride and a material that would have the highest proportion in the sintered body if the sintered body did not include the boron nitride.

4. The sensing element according to claim 3, wherein the material is alumina.

5. The sensing element according to claim 2, wherein the heat conducting layer includes the boron nitride.

6. The sensing element according to claim 5, wherein boron nitride content is 30 weight percent or more and 100 weight percent or less of a gross weight of the boron nitride and a material that would have the highest proportion in the heat conducting layer if the heat conducting layer did not include the boron nitride.

7. The sensing element according to claim 6, wherein the material is alumina.

8. The sensing element according to claim 2, wherein the catalyst layer of the sintered body includes the boron nitride.

9. The sensing element according to claim 8, wherein boron nitride content is 10 weight percent or more and 80 weight percent or less of a gross weight of the boron nitride and a material that would have the highest proportion in the catalyst layer if the catalyst layer did not include the boron nitride.

10. The sensing element according to claim 9, wherein the material is tin oxide.

11. The sensing element according to claim 2, wherein the heater coil includes a coiled coil that is covered by the sintered body.

12. The sensing element according to claim 2, wherein the heater coil includes a single coil that is covered by the sintered body.

* * * * *